United States Patent [19]

Wadsworth et al.

[11] 4,382,378
[45] May 10, 1983

[54] METHOD FOR TESTING FILTRATION EFFICIENCY

[75] Inventors: Larry C. Wadsworth, Arlington, Tex.; Wayne T. Davis, Knoxville, Tenn.

[73] Assignee: Surgikos, Inc., New Brunswick, N.J.

[21] Appl. No.: 245,815

[22] Filed: Mar. 20, 1981

[51] Int. Cl.³ .......................................... B01D 23/00
[52] U.S. Cl. ...................................................... 73/38
[58] Field of Search ............... 73/28, 38, 1 G; 55/270; 435/808; 324/71 CP

[56] References Cited

U.S. PATENT DOCUMENTS 3,478,601 11/1969 Niebergall .............................. 73/38
4,324,568 4/1982 Wilcox et al. ......................... 55/270

Primary Examiner—Stephen A. Kreitman

[57] ABSTRACT

A procedure for testing the efficiency of filtration media is disclosed. The procedure employs uniform microspheres in a latex which are suspended in an airstream and directed through the medium to be tested. The liquid in the airstream is removed from the airstream after passing through the medium, and a portion of the airstream is directed to a particle counter to count the particles in the airstream. By comparing the particles counted with and without the medium in the airstream, the efficiency of the medium can be determined.

5 Claims, 1 Drawing Figure

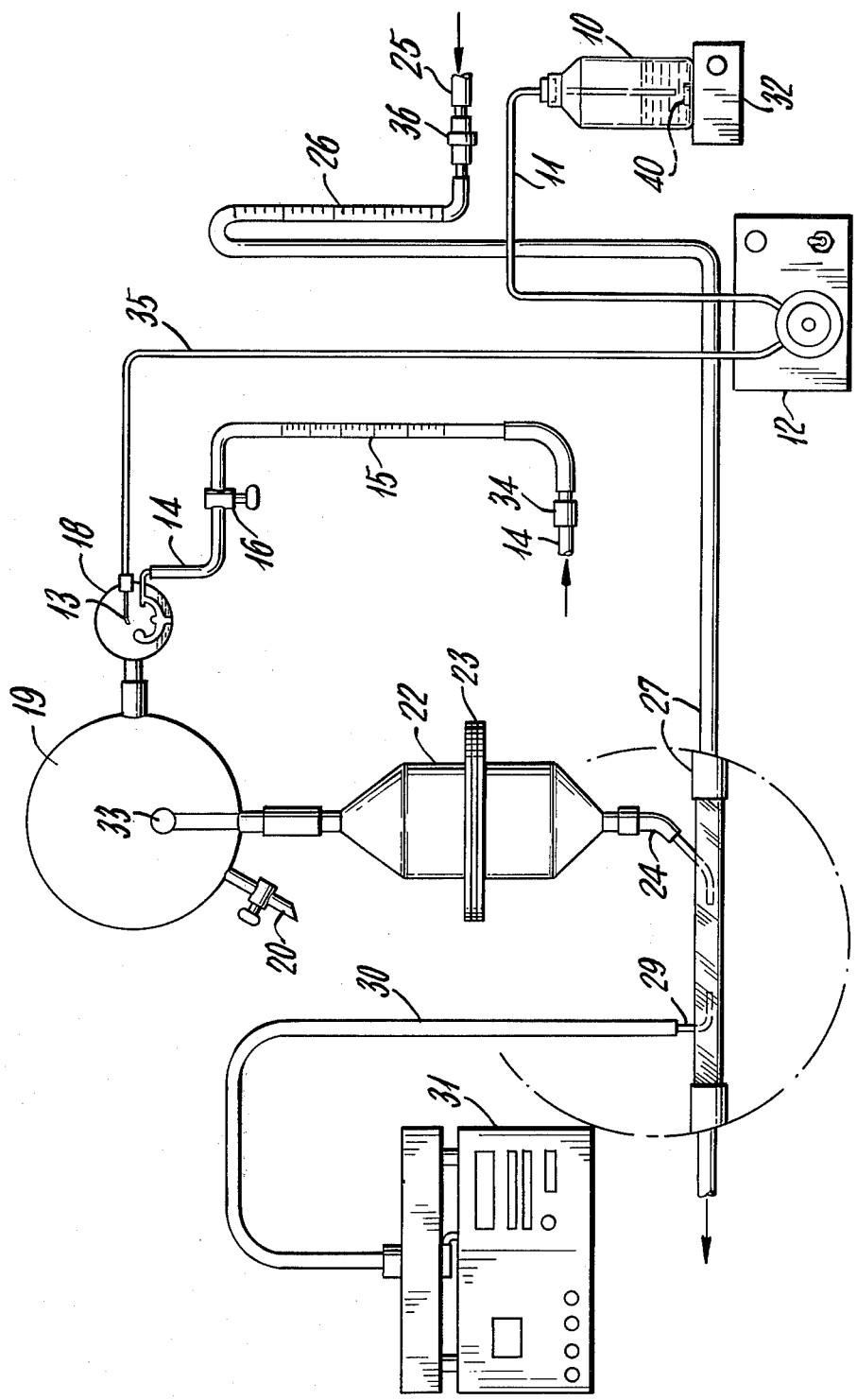

METHOD FOR TESTING FILTRATION EFFICIENCY

THE FIELD OF THE INVENTION

The present invention relates to a method to test the filtration efficiency of filtration media, particularly filtration media which are useful for the filtration of air.

PRIOR ART

Methods for testing the efficiency of air filters vary widely. Generally, these tests are not directly comparable. Tests that have previously been employed include weight tests in which the difference between the weight of a filter before and after being subjected to standardized flow of air containing standard particles is determined. A discoloration test has been employed which uses a photometric comparison between two filters, one of which is clean and the other of which is subjected to standard air flow of air containing standard particles. By comparing the colors of the filters in a device known as a Dill Dust Spot Tester, the relative efficiency rate of the filter can be determined.

A common and widely used test is the Dioctyl Phthalate (DOP) Smoke Test. This test generates smoke from dioctyl phthalate which is a particle size of approximately 0.3 microns and which is considered to be the most difficult size of particle to remove with strainer-type filters. The air containing the DOP, after passing through the filter, is passed through a penetration meter. The penetration meter consists of a chamber containing a photocell through which either the filtered or unfiltered smoke may be drawn. A beam of light shines into the chamber but is prevented by a shield from striking the photocell directly. As the smoke enters the chamber, light is refracted by the smoke around the shield and falls on the photocell. An electrical impulse is amplified and registers directly as the percentage of penetration of the DOP smoke.

Another test employed to test filtration efficiency is the Polydispersed DOP Method. In this test, the DOP aerosol contains particles which range in size from 0.3 microns to 3 microns. An air stream containing the DOP particles is drawn directly through the medium to be tested. A sample of the airstream before and after the filtration medium is directed to a stectrophotometer which directly compares the DOP concentration before and after the filtration medium. The concentrations of DOP can be directly converted into percent efficiency of the filtration medium.

A standard test which is widely used, particularly for medical products, is the Bacterial Filtration Efficiency Test (B.F.E.). This test is run in the following manner. Staphylococcus aureus bacteria is nebulized into a spray mist and forced through an aperture in a closed conduit. The bacteria passing through the aperture is trapped on a Millipore Filter and then innoculated on agar plates. The same procedure is repeated with the filtration medium to be tested blocking the aperture of the conduit. After a period of 24–48 hours, the bacteria colonies are counted. The efficiency of the filtration medium is determined by comparing the colony count on the plates with and without the filtration medium in the aperture. The B.F.E. Test is widely used in medical products but is time consuming as it takes 24–48 hours to complete the test. Because this test is biological, it is also difficult to obtain reproducible results.

All of the physical tests mentioned above utilize aerosols to challenge the filter medium. With the exception of the Bacterial Filtration Efficiency Test, these aerosols are either completely solid or completely liquid but are not combinations of solid and liquid systems, as is the Bacterial Filtration Efficiency Test. Examples of the dry or solid aerosols employed are silica, selenium, amorphous sodium chloride, quartz dust, methylene blue, dried latex particles and fly ash. Liquid aerosols that have been utilized include paraffin oil mist and dioctyl phthalate. The latex particles that are used in the present test have previously been utilized in other procedures to determine filtration efficiency. However, in these previous methods that latex particles were dried by evaporation with dilution air or by other means prior to their use in challenging the filtration medium to be tested.

None of the filtration efficiency test systems previously employed have been able to be correlated with the Bacterial Filtration Efficiency Test.

SUMMARY OF THE INVENTION

The present invention relates to a filtration efficiency test which employs a combination of liquid and solid particles to test the efficiency of the filter. The present test has been found to be able to be correlated with the Bacterial Filtration Efficiency Test. The test of the present invention requires only minutes to perform, which makes it very suitable to be used as a quality control test in the manufacture of filtration medium. The medium can be tested as it is being produced to determine if it meets the filtration efficiency standards set by the manufacturer.

The present invention employs a combination of both liquid, in the form of water, and solid components to challenge the filter medium and determine its efficiency. The test more accurately duplicates the B.F.E. Test, which in effect uses an aerosol which is a combination of liquid, water, and solid components in the form of bacteria. It is believed that the transport mechanism of the bacteria through the pores of the filtration medium in this test is different than the transport medium in test systems in which completely liquid or completely dry aerosols are utilized.

In the present test, an aerosol of latex comprising polymer particles in water is diluted in an air stream and directed through the filtration medium to be tested and then to an optical particle counter to count the particles that have penetrated the filtration medium. Before the air stream is directed to the particle counter, the liquid water in the system is evaporated and removed from the air stream. The particle counter, therefore, counts only the solid particles that have penetrated the filtration medium and not the liquid water droplets from the latex. The filtration medium, however, is challenged by a combination of liquid and solid components which more accurately duplicate the Bacterial Filtration Efficiency Test.

DESCRIPTION OF THE DRAWINGS

The FIGURE is a schematic illustration of the testing equipment utilized in the present invention.

DETAILED DESCRIPTION OF THE INVENTION

In the apparatus shown in the FIGURE, there is a container 10 which contains a latex hydrosol which is a suspension of uniform particles in water. These particles may range in size from approximately 0.1 micrometers to approximately 100 micrometers. Genterally, the particle size selected to test any particular filtration medium should correspond as closely as possible to the particle size of the particulate matter that will be encountered during the actual use of the filtration medium. In testing the filtration efficiency of medical products, such as surgical face masks, a latex particle of 0.804 micrometers has been found to give excellent correlation to the above-mentioned B.F.E. Test which employs Staphylococcus aureus bacteria which have a mean diameter of 0.8 to 1 micrometers.

The solid particles of the latex are polystyrene, polyvinyltoluene, copolymers of vinyltoluene and tertiary butylene, styrene and butadiene, styrene and vinyltoluene or styrene and divinylbenzene prepared by emulsion polymerization. The latex particles can be obtained from the Dow Diagnostics Division of Dow Chemical Company. The stock latex hydrosol is at a concentration of 10% to 30% solids. A small amount of the stock solution, 0.5 to 3 milliliters, is diluted with distilled water to form 1,000 milliliters of diluted latex which is added to a container 10. The desired concentration of latex particles will depend on the latex particle size and the desired concentration of particles in the air stream to the filtration medium to be tested. As the size of the particles increases, the concentration must be increased to give the same number of particles in the air stream. In testing surgical face masks 1 to 2 milliliters of a 10% latex solids hydrosol is diluted to 1,000 milliliters. The latex in the container 10 is continually agitated by magnetic stirrer 32 which acts on a metallic bar 40 in container 10. There is a tube 11 which is connected to a peristaltic pump 12 which draws the latex hydrosol from the container 10 and directs it through tube 35 to a nebulizer 18. The nebulizer is of a standard construction available from the Fisons Corporation. The latex is introduced into the nebulizer through an 18-gauge syringe needle 13. Air enters the nebulizer through conduit 14 through a flow meter 15 to the nebulizer 18. There is a stopcock 16 to direct the air flow to the nebulizer. The nebulized particles flow from the nebulizer to a mixing air chamber 19 which is a large glass sphere. Large water droplets in the air stream will fall to the bottom of the mixing chamber. Portions of the air which contain the fine aerosol particles will flow through "T" tube 33 (shown in an end view) into a sample holder 22. There is an opening 23 in the sample holder which allows samples of filtration medium to be inserted into the sample holder. There is a drain 20 in the mixing chamber to allow the chamber to be emptied of any liquid that might accumulate in the chamber. The particles in the air leave the sample holder through conduit 24 and enter a drying tube 27. A portion of the drying tube is shown in an enlarged view in the drawing. Dilution air enters the drying tube 27 from the inlet 25, and the flow rate of this air is measured by a flow meter 26. The air flow to the drying tube is controlled by a valve which is not shown on the drawing. There is a conduit 29 within the drying tube which samples portions of the air in the drying tube. This air is directed through conduit 30 and drawn into the particle counter 31 by a pump within the counter. The function of the drying tube 27 is to evaporate any liquid particles which pass through the filter sample leaving primary dried latex microsphere to be counted by the particle counter. The dilution air flow rate should be adjusted to give isokinetic flow into the particle counter. That is, the flow rate in the drying tube 27 should be the same flow rate as the flow rate in the conduit 30 leading to the particle counter 31. There is a millipore filter in a holder 34 and 36 at the inlet of the air conduits 14 and drying tube 27 to remove particles from the air before the air enters the testing apparatus.

The test apparatus is operated in the following manner. The peristaltic pump is started at the same time that air flow through conduit 14 is directed to the nebulizer 18. The air flow rates of the inlet air to the nebulizer should be approximately 1 to 6 liters per minute. The air from the inlet 14 is filtered through a Millipore Filter 34 before it enters the nebulizer. The flow rate is adjusted by a valve which is not shown and can be accurately controlled by measurement with a flow meter 15. The solid particles in the latex are nebulized and pass through the sample holder, which does not contain a sample of a filter medium to be tested. The dilution air, which flows through drying tube 27, should be at a much higher rate than the inlet air to the nebulizer. Air flow rates of approximately 50 liters per minute for the dilution air have been found to give good results. The particle counter 31, which is a comercially available counter such as the Royco Model #225 with a #518 module furnished by the Pacific Scientific Company, has been found to give excellent and reproducible results. The counter is started, and the count of the particles is determined after a predetermined time has elapsed.

The filter medium to be tested is inserted into the sample holder and the apparatus is again run to determine the number of particles that have come through the filtration medium. A comparison of the number of particles that are counted in a given time period, without and with the filtration sample in place, is a determination of the filtration efficiency of the particular sample.

The time elapsed from the start of the flow of air containing the latex particles through the filtration medium to the start of the particle counter for the counting sequence is the presaturation time. An ample presaturation time, 15 seconds to 3 minutes, has been found to be advantageous in giving good correlation between the present test and the Bacterial Filtration Efficiency Test. Presaturation times of from 15 seconds to 2 minutes have been found to be adequate. Higher presaturation times can be employed if desired. The presaturation time should be consistent in determining the filtration efficiency of paired samples for comparison purposes.

EXAMPLE I

In the following Table I, the results of filtration efficiency testing of filtration media using the B.F.E. Test and the Polydispersed DOP Test Method are reported. The results reported are the average of three to five specimens of the filtration medium tested. It is clear from the results reported that the correlation between the B.F.E. Test and the Polydispersed DOP Test is very poor.

TABLE I

| | In Vitro B.F.E. | |
| --- | --- | --- |
| Sample NO. # | In Vitro B.F.E. (%) | Polydisperse DOP Filtration (%) |
| 1 | 36.6 | 36.9 |
| 2 | 42.3 | 36.9 |
| 3 | 63.6 | 36.9 |
| 4 | 73.0 | 93.7 |

TABLE I-continued

| Sample NO. # | In Vitro B.F.E. (%) | Polydisperse DOP Filtration (%) |
|---|---|---|
| 5 | 81.9 | 68.4 |
| 6 | 85.0 | 60.2 |
| 7 | 90.6 | 49.9 |
| 8 | 95.0 | 60.2 |
| 9 | 98.9 | 92.0 |
| 10 | 91.7 | 59.2 |

EXAMPLE II

The following Table II compares the filtration efficiency results of the present invention at different pre-saturation times with the results obtained by the B.F.E. Test previously described. Four samples of each filter medium were tested, and the value reported is the average of the four samples. It is evident from the results reported in Table I that these better correlate to the B.F.E. Test of the present invention than the Polydispersed DOP Test shown in Example I, Table I.

TABLE II

| In Vitro B.F.E. | F.E.T. 15 Second | F.E.T. 1¼ min. | F.E.T. 2¼ min. |
|---|---|---|---|
| 48.5 | 0.0 | 16.3 | 27.8 |
| 49.5 | 12.5 | 34.2 | 49.0 |
| 52.3 | 3.0 | 23.8 | 37.9 |
| 56.7 | 33.1 | 49.3 | 59.5 |
| 72.3 | 55.4 | 63.4 | 70.5 |
| 76.8 | 57.7 | 65.5 | 71.0 |
| 90.3 | 81.7 | 86.0 | 88.3 |
| 92.5 | 78.3 | 82.6 | 83.9 |
| 91.7 | 93.1 | 97.5 | 98.4 |
| 98.9 | 97.6 | 99.1 | 99.5 |

We claim:

1. A method of determining the filtration efficiency of a filtration medium comprising:
   (a) suspending in an airstream a uniform latex of polymeric microspheres in water;
   (b) directing the suspended latex microspheres through an empty filter holder;
   (c) drying the airstream to remove the liquid portion of the latex;
   (d) directing a portion of the air stream through a particle counter to determine the number of particles in the air stream;
   (e) inserting a filtration medium in the filter holder;
   (f) directing the suspended latex microspheres through the filter holder containing the filtration medium;
   (g) drying the airstream to remove the liquid portion of the latex;
   (h) directing a portion of the air stream through a particle counter to determine the number of particles in the air stream; whereby the efficiency of the filtration medium can be determined by comparing the particles counted with the filtration medium in the filter holder and the particles counted without the filtration medium in the filter holder.

2. The method of claim 1 in which the microspheres are particles made from a polymer selected from the group consisting of polystyrene, polyvinyltoluene, copolymers of vinyltoluene and tertiary butylene, styrene and butadiene, styrene and vinyltoluene and styrene and divinylbenzene.

3. The method of claim 1 in which the microspheres have a diameter of from 0.6 to 2 microns.

4. The method of claim 1 in which the latex microspheres are directed through the filtration medium for a period of from 15 seconds to 120 seconds before the particles are counted by the particle counter.

5. The method of claim 2 in which the microspheres are polystyrene.

* * * * *